(12) United States Patent
Prosise

(10) Patent No.: US 8,137,658 B2
(45) Date of Patent: Mar. 20, 2012

(54) TOOTH WHITENING COMPOSITIONS

(75) Inventor: William E. Prosise, Ramsey, NJ (US)

(73) Assignee: ISP Investments Inc., Wilmington, DE (US)

( * ) Notice: Subject to any disclaimer, the term of this patent is extended or adjusted under 35 U.S.C. 154(b) by 1685 days.

(21) Appl. No.: 11/168,163

(22) Filed: Jun. 28, 2005

(65) Prior Publication Data

US 2006/0292091 A1 Dec. 28, 2006

(51) Int. Cl.
*A61K 8/22* (2006.01)

(52) U.S. Cl. .......... 424/53; 510/296; 510/392; 510/406; 510/418; 510/439; 525/60

(58) Field of Classification Search .................. None
See application file for complete search history.

(56) References Cited

U.S. PATENT DOCUMENTS

| | | | |
|---|---|---|---|
| 4,942,034 A * | 7/1990 | Hill et al. ............... | 424/401 |
| 5,008,093 A | 4/1991 | Merianos | |
| 5,008,106 A | 4/1991 | Merianos et al. | |
| 5,066,488 A | 11/1991 | Merianos et al. | |
| 5,077,047 A | 12/1991 | Biss et al. | |
| 5,108,742 A | 4/1992 | Merianos | |
| 5,122,370 A | 6/1992 | Merianos et al. | |
| 5,130,124 A | 7/1992 | Merianos et al. | |
| 5,159,033 A | 10/1992 | Merianos et al. | |
| 5,177,113 A | 1/1993 | Biss et al. | |
| 5,183,901 A | 2/1993 | Login et al. | |
| 5,190,749 A | 3/1993 | Login et al. | |
| 5,206,385 A | 4/1993 | Login et al. | |
| 5,312,619 A | 5/1994 | Shih et al. | |
| 5,364,601 A | 11/1994 | Salpekar | |
| 5,423,337 A | 6/1995 | Ahlert et al. | |
| 5,645,848 A | 7/1997 | De et al. | |
| 5,667,753 A | 9/1997 | Jacobs et al. | |
| 5,674,436 A | 10/1997 | Breitenbach et al. | |
| 5,674,450 A | 10/1997 | Lin et al. | |
| 5,680,876 A | 10/1997 | Hasham et al. | |
| 5,698,182 A | 12/1997 | Prencipe et al. | |
| 5,718,886 A | 2/1998 | Pellico | |
| 5,753,770 A | 5/1998 | Breitenbach et al. | |
| 5,770,182 A | 6/1998 | Fischer et al. | |
| 5,785,934 A | 7/1998 | Jacobs et al. | |
| 5,820,841 A | 10/1998 | Chen et al. | |
| 5,846,570 A | 12/1998 | Barrow et al. | |
| 5,876,666 A | 3/1999 | Lin et al. | |
| 5,879,691 A | 3/1999 | Sagel et al. | |
| 5,891,453 A | 4/1999 | Sagel et al. | |
| 5,894,017 A | 4/1999 | Sagel et al. | |
| 5,922,307 A | 7/1999 | Montgomery | |
| 5,989,526 A | 11/1999 | Aaslyng et al. | |
| 5,989,569 A | 11/1999 | Dirksing et al. | |
| 6,045,811 A | 4/2000 | Dirksing et al. | |
| 6,096,328 A | 8/2000 | Sagel et al. | |
| 6,106,812 A | 8/2000 | Prencipe et al. | |
| 6,136,297 A | 10/2000 | Sagel et al. | |
| 6,221,341 B1 | 4/2001 | Montgomery | |
| 6,312,670 B1 | 11/2001 | Montgomery | |
| 6,322,773 B1 | 11/2001 | Montgomery | |
| 6,331,292 B1 | 12/2001 | Montgomery | |
| 6,419,906 B1 | 7/2002 | Xu et al. | |
| 6,500,408 B2 | 12/2002 | Chen | |
| 6,503,486 B2 | 1/2003 | Xu et al. | |
| 6,528,470 B1 | 3/2003 | Ha et al. | |
| 6,555,020 B1 | 4/2003 | Chadwick et al. | |
| 6,576,227 B1 | 6/2003 | Montgomery | |
| 6,669,930 B1 | 12/2003 | Hoic et al. | |
| 6,682,721 B2 | 1/2004 | Kim et al. | |
| 6,689,344 B2 | 2/2004 | Chang et al. | |
| 6,692,727 B1 | 2/2004 | Yue et al. | |
| 6,730,316 B2 | 5/2004 | Chen | |
| 6,770,266 B2 | 8/2004 | Santarpia, III et al. | |
| 6,780,401 B2 | 8/2004 | Chang et al. | |
| 6,893,629 B2 | 5/2005 | Prosise et al. | |
| 2002/0006387 A1 | 1/2002 | Sagel et al. | |
| 2002/0012685 A1 | 1/2002 | Sagel et al. | |
| 2002/0061283 A1 | 5/2002 | Montgomery | |
| 2002/0064564 A1 | 5/2002 | Montgomery | |
| 2002/0068041 A1 | 6/2002 | Montgomery | |
| 2002/0131937 A1 | 9/2002 | Montgomery | |
| 2003/0072722 A1 | 4/2003 | Nathoo | |
| 2003/0211052 A1 | 11/2003 | Georgiades | |
| 2004/0062724 A1 | 4/2004 | Moro et al. | |
| 2004/0191188 A1 | 9/2004 | Freedman | |
| 2005/0036956 A1 | 2/2005 | Fei et al. | |

* cited by examiner

*Primary Examiner* — Walter Webb

(74) *Attorney, Agent, or Firm* — Thompson Hine LLP

(57) ABSTRACT

A liquid, substantially anhydrous tooth whitener composition for delivery of a tooth-whitening amount of active whitening ingredient onto teeth, with effective bioadhesion and retention thereof, and, thereupon, sufficient penetration of the ingredient through the tooth enamel, providing efficacious bleaching of stained teeth.

8 Claims, 1 Drawing Sheet

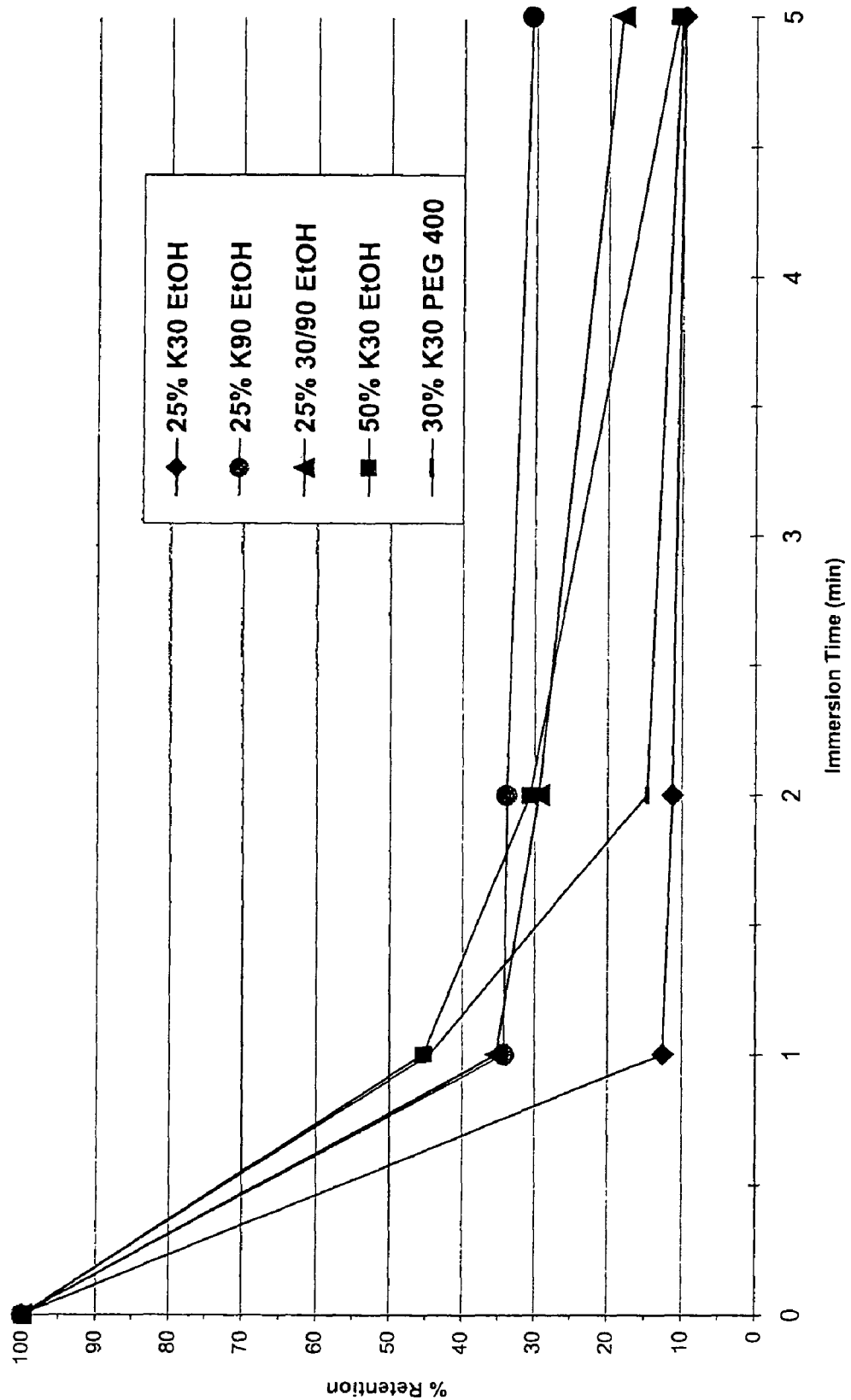

TOOTH WHITENING COMPOSITIONS

BACKGROUND OF THE INVENTION

1. Field of the Invention

This invention relates to tooth whitening compositions, and, more particularly, to a liquid, substantially anhydrous tooth whitening composition for effective delivery of a tooth whitening ingredient onto teeth, which exhibits excellent bioadhesion and retention thereon, advantageous penetration through tooth enamel, superior bleaching of stained teeth, and a predetermined Brookfield viscosity which provides for multiple methods of delivery of the tooth whitening ingredient onto teeth.

2. Description of the Prior Art

Since the early 1980s, the tooth whitening industry has grown from a scenario in which one could only receive tooth whitening treatments in a dental office to the scenario that exists today in which numerous competitors sell over-the-counter tooth whitening systems including delivery systems such that the average consumer can whiten their teeth in their own home without medical supervision.

Numerous delivery systems have become popular and well known including those employing strips coated with the tooth whitening substance, trays filled with tooth whitener, tooth whiteners incorporated into toothpaste, and other paint-on applicators such as those analogous to felt tip pens, and others using brushes with bristles and foam-type brush applicators. Over-the-counter whiteners today fall into three categories—trays and gels, strips and paint-on whiteners.

Tray and gel systems are designed for the user to fill the flexible tray with the whitening formulation and this is placed on the teeth. The gel extrudes out of the tray on the gingival and the mucosa with a great chance of soft tissue irritation. Strips are placed on the teeth with a good portion of the strip laying on the gingival area and also causing irritation.

A successful tooth whitening composition requires that the following parameters be favorable:

(1) A sufficient amount of activated active ingredient, e.g. $H_2O_2$ present in and delivered by the composition;

(2) an enhanced degree of retention of the composition onto teeth; i.e. its bioadhesion, which is determined by the ratio of its cohesive energy to surface energy;

(3) a favorable degree of penetration of the composition into the tooth enamel;

(4) a suitable viscosity to deliver the composition by selected desirable means; and, (5) efficacy of bleaching of stained teeth enamel by the composition.

Accordingly, it is the object of this invention to provide a tooth whitener composition having, in combination:

(1) a predetermined concentration of active $H_2O_2$ in a film-forming complex; which provides for;

(2) effective bioadhesion/retention of the composition on teeth;

(3) advantageous penetration of the composition into the tooth enamel;

(4) a predeterminable viscosity to deliver the composition onto teeth by one or more suitable delivery means; and (5) excellent bleaching action on stained teeth.

The following patents illustrate suitable active tooth whitening substances and delivery systems therefor: U.S. Pat. Nos. 5,077,047, U.S. Pat. No. 5,108,742; U.S. Pat. No. 5,122,370; U.S. Pat. No. 5,130,124; U.S. Pat. No. 5,183,901; U.S. Pat. No. 5,190,749; U.S. Pat. No. 5,206,385; U.S. Pat. No. 5,312,619; U.S. Pat. No. 5,989,569; U.S. Pat. No. 6,669,930; U.S. Pat. No. 6,770,266; U.S. Pat. No. 6,893,629 and U.S. 2003/0203338A1.

These and other objects and features of the invention will be made apparent from the following description.

IN THE DRAWINGS

The FIG. 1 is a plot of % Retention vs. Immersion Time for the tooth whitening composition of the invention on hydroxyapatite.

SUMMARY OF THE INVENTION

What is described herein is a liquid, substantially anhydrous tooth whitener composition for effective delivery of a tooth-whitening amount of active whitening ingredient onto teeth, excellent bioadhesion and retention of said ingredient on teeth, advantageous penetration of said ingredient through tooth enamel, and effective bleaching of stained teeth, comprising, by weight, (a) 10% to 75% of a complex which is (i) a mixture of 78 to 90% of water soluble polyvinylpyrrolidone (PVP) having a molecular weight corresponding to K-12 to K-120 values, and (ii) 10 to 22% of $H_2O_2$; providing 1 to 20% of active $H_2O_2$ onto a tooth surface;

(b) 0 to 20% of PVP K-60 to K-90, said PVP being present in said composition when the PVP in said complex has a K-value of less than 30, and/or the amount of PVP therein is less than 20%, and (c) 30 to 90% of a substantially anhydrous solvent, said composition having, in combination, a Brookfield viscosity of 50 to 2000 cps, an in vitro bioadhesion and retention on hydroxyapatite of at least 10% after 5 minutes while immersed in water, and a bleaching efficacy defined by $\Delta E$ values of at least 5 in the CIE (L*a*b*) color scale.

Suitably, the tooth whitener composition of the invention includes (a) PVP K-30 to K-90. When present, the PVP in (b) is suitably K-90.

Alternatively, the tooth whitener composition herein includes PVP K-90 in (a), and (b) is absent.

Preferably the amount of the complex (a) in the composition is 20 to 60% and (b) is 0.1-10%.

Preferably the solvent in the tooth whitener composition is ethanol in an amount of 65 to 80 wt. % of the composition.

Preferably, the tooth whitener composition of the invention has a viscosity of 75 to 1500 cps, most preferably 100 to 800 cps.

1. Amount of Activated $H_2O_2$

In one embodiment of the invention, the complex in the tooth whitening composition is available as the commercial product PEROXYDONE® (ISP), which is made up of, by weight, 80-83%, of water soluble polyvinylpyrrolidone (PVP), e.g. K-15/K-30/K-90, and 17-20%, by weight, hydrogen peroxide ($H_2O_2$).

This PVP-$H_2O_2$ complex, with or without added (b) PVP, e.g. Plasdone® K-90 (ISP), to increase its viscosity, is mixed with a suitable proportion of a solvent, e.g. absolute ethanol. When applied to the surfaces of the teeth of the user, the ethanol immediately begins to evaporate resulting in a marked increase in the concentration of $H_2O_2$ thereby enhancing the whitening power of the formulation.

Typical tooth whitening compositions of the invention are shown in Tables 1 and 2 below.

TABLE 1

| Ingredient | EXAMPLE NO. | | | | | | | | |
|---|---|---|---|---|---|---|---|---|---|
| | 1 | 2 | 3 | 4 | 5 | 6 | 7 | 8 | 9 |
| Peroxydone ® K-30 | 23.3 | 27.77 | 40.0 | 37.5 | 35.0 | 23.3 | 27.8 | 40.0 | 23.3 |
| % $H_2O_2$ | 4.2 | 5.1 | 8.0 | 7.5 | 7.0 | 4.7 | 5.6 | 7.8 | 4.3 |
| Plasdone ® K-90 | 5.00 | 3.75 | — | — | — | 3.50 | 2.50 | — | 4.75 |
| Ethanol (Abs.) | 71.2 | 67.98 | 59.5 | 62.0 | 64.5 | 62.9 | 69.1 | 59.4 | 71.35 |
| Brookfield Viscosity, cPs | 246 | 244 | 280 | 172 | 120 | 117 | 124 | 217 | 206 |

TABLE 2

| Ingredient | EXAMPLE NO. | | | | | | | | |
|---|---|---|---|---|---|---|---|---|---|
| | 10 | 11 | 12 | 13 | 14 | 15 | 16 | 17 | 18 |
| Peroxydone ® K-30 | 27.78 | 17.50 | 20.00 | 62.50 | 20.00 | 25.00 | 40.00 | 40.00 | 40.00 |
| Peroxydone ® K-90 | — | 7.50 | 5.00 | 3.75 | 20.00 | 15.00 | — | — | — |
| % $H_2O_2$ | 5.3 | 5.0 | 4.8 | 13.1 | 8.0 | 7.9 | 7.9 | 7.8 | 7.9 |
| Plasdone ® K-90 | 3.50 | — | — | — | — | — | 5.00 | 10.00 | 7.50 |
| Ethanol (Abs.) | 68.12 | 74.58 | 74.5 | 66.75 | 59.5 | 59.5 | 54.5 | 49.5 | 52.0 |
| Brookfield Viscosity, cPs | 195 | 272 | 171 | 515 | >1000 | ~1000 | 179 | 790 | 488 |

TABLE 3

| Example No. | Ingredients |
|---|---|
| 19 | 25% Peroxydone K-30 in Ethanol (18.7% $H_2O_2$) |
| 20 | 25% Peroxydone K-90 in Ethanol (17.5% $H_2O_2$) |
| 21 | 12.5% Peroxydone K-30 and 12.5% Peroxydone K-90 in Ethanol |
| 22 | 50% Peroxydone K-30 in Ethanol |
| 23 | 30% Peroxydone K-30 in PEG 400 |

2. Viscosity of Composition

As is shown in Tables 1 and 2, when the PVP ingredient in the complex includes PVP having a K-value of K-90, and the complex is present in an amount of at least 15% of the composition, the viscosity of the composition is 1000 cps or above. On the other hand, when the K-value of the PVP in the complex is K-30 or lower, and its amount therein is 40% or lower, the viscosity of the composition is less than 300 cps.

An increase in the Plasdone® K-90 content of the composition increases the viscosity of the composition significantly.

3. Bioadhesive/Retention of Composition on Teeth

The relative retention capacity of a test formulation on tooth surfaces can be measured by weight difference from the surface of a hydroxyapatite (HAP) plate that has been coated with the formulation and immersed in artificial saliva. An in-vitro test for formula weight retention on HAP is described below.

These in-vitro tests for formulation efficacy can be used to collectively determine the relative performance of paint-on teeth bleaching compositions.

Formula Retention Test a) Accurately tare HAP-coated glass plate to 3 decimal places.
b) Paint HAP surface with a single coat of product, wait 30 seconds, and reweigh (3 dec.).
c) Place coated HAP in one liter of artificial saliva for 0, 1, 2 and 5 minutes time.
d) Remove each slide after its specified time, dry to constant weight, and weigh.
e) Determine initial product weight, and product weight after 1, 2 and 5 minutes submersion in artificial saliva.
f) Calculate percent retained on HAP versus time.

The FIGURE presents the percent retention on hydroxyapatite (HAP) versus immersion time of the teeth whitening formulations of the invention (Examples 19-23).

After five minutes immersion time, the 25% K-90 EtOH formulation is the best retained on HAP. The blend of K-90 and K-30 also exhibits effective retained time on HAP (at five minutes), as did the 50% K-30 EtOH formulation.

4. Bleaching Efficacy

The stain bleaching efficacy of the teeth whitening products compositions of the invention is determined by the rate of peroxide bioadhesion into the teeth and retention of the vehicle on the tooth surface. Two recent in-vitro methods to measure bleaching activity of such compositions were developed by Colgate-Palmolive Company and published in a poster session at the 2004 meeting of the Intl. Assoc, for Dental Research*.

*Subramanyam, R.; Cameron, R; Colgate Palmolive Co.; "Comparative Delivery of Bleaching Agent from At-home Whitening Products"; Poster #3527; Presented at IADR Annual Meeting; Honolulu, Hi.; Mar. 10-13, 2004

These methods are based on a dye compound that acts as a surrogate for teeth stain on the exterior of teeth (extrinsic stain) or within the teeth (intrinsic stain). The rate of bleaching of a fixed amount of dye can thus indicate the peroxide release rate from a formulation. Additionally, the relative rate of absorption or penetration by the peroxide from the formulations can be determined by the bleaching of a previously dyed porous substance.

Formulation bleaching efficacy also can be determined by measuring the instrumental color difference of stained HAP disks before and after bleaching. A test was developed that measures the L*a*b* color of tea-stained disks before staining, after staining, and after bleaching. Color differences (Δ E) as a result of bleaching with different formulations can be determined mathematically.

Three separate bleaching efficacy tests were developed. The following procedures are presented for each separate test. Five simple Peroxydone®-based formulas of the invention were evaluated for performance in each test method. The hydrogen peroxide content was determined by permanganate titration.

Table 4 lists the averaged L*a*b* color results of each two disk set before staining, after staining and after staining and bleaching with each of the five prototype whitening formulations. Δ E color differences between each variable and no stain were calculated. Additionally, Δ E color differences realized by bleaching were calculated. These are Δ E's between stained disked before and after bleaching.

TABLE 4

| | B/4 Bleaching | | | | |
|---|---|---|---|---|---|
| Dry | Stain Only | Stain Only | Stain Only | Stain Only | Stain Only |
| L | 80.97 | 81.28 | 79.87 | 79.08 | 81.99 |
| A | 4.29 | 4.19 | 4.56 | 4.33 | 4.37 |
| B | 9.15 | 9.09 | 8.66 | 8.94 | 9.04 |
| E vs No Stain | 19.388 | 19.073 | 20.174 | 20.902 | 18.522 |

| | After Bleaching | | | | |
|---|---|---|---|---|---|
| Dry | 25% K-30 EtOH | 25% K-90 EtOH | 25% 30/90 EtOH | 50% K-30 EtOH | 30% K-30 PEG 400 |
| L | 89.69 | 84.11 | 81.54 | 91.71 | 89.49 |
| A | 0.98 | 2.51 | 4.11 | 0.15 | 1.28 |
| B | 4.41 | 15.52 | 18.88 | 2.76 | 3.34 |
| E vs No Stain | 8.938 | 20.646 | 25.106 | 6.242 | 8.711 |
| Δ E - Stain Removal by Bleaching | 10.464 | 7.218 | 10.367 | 14.668 | 9.918 |

HAP Disk Bleaching Test
- a) Tea Stain Solution Preparation—Ten (10) Lipton tea bags (25.4 g including paper) were placed in 215 g D.I. water at 195 F and held for 25 minutes. Bags were removed and stain solution was immediately used.
- b) Formation of Pellicle and Uptake of Stain onto HAP Disks—Each disk was covered with 2 g of 1% mucin supernatant and incubated overnight (20 hours) in a test tube at 37°C with gentle shaking using a vortex mixer at about a 400 speed. This forms a mucin coating on the disk that simulates a salivary pellicle.
- c) Staining Disks—Each disk was removed from the mucin supernatant and rinsed by dipping in a large excess of D.I. water three times. All disks, except two (unstained), were individually placed in 2 ml of tea stain concentrate in test tubes, and incubated at 37°C for one (1) hour with gentle shaking at a speed of 300. The disks were each removed from the stain, rinsed three (3) times by dipping in excess D.I. water and air-dried overnight.
- d) All disks were individually numbered and separated into two disk sets. The color of each disk was measured by Minolta Spectrophotometer over the entire visual spectrum and by L*, a*, b*. Colors were averaged for each of the two-disk sets.
- e) Stained disks were hydrated in artificial saliva for four hours, and placed flat in a petri plate partially submerged in artificial saliva.
- f) Disk top surfaces were blotted dry, while partially submerged, and each two-disk set was painted with a single coat of teeth whitener (bleach) and held (covered, partially submerged) for 30 minutes.
- g) Disks were removed from artificial saliva, rinsed three times in D.I. water, wiped dry, and placed in a desiccator overnight (20 hours) to dry.
- h) The color of each bleached disk was measured by Minolta Spectrophotometer (as d above). Colors were averaged for each of the two-disk sets.
- i) Average colors were plotted and appropriate Δ E values (mathematical color differences) were calculated. L*, a*, b* color and Δ E values are given below.

Reflected Color by Hunter Colorimeter

Commission Internationale de l'Eclairage (CIE) uses L*a*b* scale
L is lightness 0=black, 100=pure white
a is yellow (+) and blue (−)
b is red (+) and green (−)
Total Color Difference (ΔE) between a sample and standard (or control)

$$\Delta E = ((\Delta L)^2 + (\Delta a)^2 + (\Delta b)^2)^{0.5}$$

Reference: Hunter Associates Laboratory, Reston, Va.

While the invention has been described with particular reference to certain embodiments thereof, it will be understood that changes and modifications may be made which are within the skill of the art.

What is claimed is:

1. A liquid, substantially anhydrous tooth whitener composition for delivery of a tooth-whitening amount of active whitening ingredient onto teeth, with effective bioadhesion and retention thereof, and, thereupon, sufficient penetration of said ingredient through the tooth enamel, providing efficacious bleaching of stained teeth, comprising, by weight,
   (a) 10% to 75% of a complex which is (i) a mixture of 78 to 90% of water soluble polyvinylpyrrolidone (PVP) having K-values of K-12 to K-120 and (ii) 10 to 22% of $H_2O_2$; releasing 1 to 20% of active $H_2O_2$ from said complex onto a tooth surface;
   (b) 0 to 20% of PVP K-60 to K-90, said PVP being present in said composition at a K-value of the PVP in said complex of less than 30, and/or the amount of PVP therein is less than 20%, and
   (c) 30 to 90% of anhydrous ethanol, said composition having a Brookfield viscosity measured at 25° C. of 50 to 10,000 cps, an in vitro bioadhesion/retention on hydroxyapatite (HAP) of at least 10% after 5 minutes while immersed in water, and a bleaching efficacy defined by ΔE values in the CIE (L*a*b*) color scale of at least 5.

2. A tooth whitener composition according to claim 1 wherein the PVP in (a) is PVP K-30.

3. A tooth whitener composition according to claim 1 wherein the PVP in (b) is PVP K-90.

4. A tooth whitener composition according to claim 1 wherein the PVP in (a) is K-90.

5. A tooth whitener composition according to claim 1 wherein said amount of in (c) is 65 to 80%.

6. A tooth whitener composition according to claim 1 having a viscosity measured at 25° C. of 75-1500 cps.

7. A tooth whitener composition according to claim 6 having a viscosity measured at 25° C. of 100 to 800 cps.

8. A tooth whitener composition according to claim 1 wherein the amount of said complex comprises: (a) 20 to 60%, and (b) 0.1-10%.

* * * * *